United States Patent

Clough

[11] Patent Number: 4,496,388
[45] Date of Patent: Jan. 29, 1985

[54] TRIAZOLYLALKANETRIOL DERIVATIVES

[75] Inventor: John M. Clough, Buckinghamshire, England

[73] Assignee: Imperial Chemical Industries PLC, London, England

[21] Appl. No.: 402,796

[22] Filed: Jul. 27, 1982

[30] Foreign Application Priority Data

Aug. 19, 1981 [GB] United Kingdom ................ 8125378
Feb. 9, 1982 [GB] United Kingdom ................ 8203708
Apr. 1, 1982 [GB] United Kingdom ................ 8209705

[51] Int. Cl.$^3$ .................... A01N 43/50; A01N 43/64; C07D 233/60; C07D 249/08
[52] U.S. Cl. ................................... 71/76; 71/92; 548/101; 548/262; 548/336; 548/341; 549/555; 549/556; 568/42; 568/43; 568/335; 568/336; 568/414; 568/415; 514/184; 514/383
[58] Field of Search ............... 548/101, 262, 341, 336; 71/76, 92; 424/245, 269, 273 R

[56] References Cited

FOREIGN PATENT DOCUMENTS

| | | | |
|---|---|---|---|
| 0061835 | 10/1982 | European Pat. Off. ............ | 424/269 |
| 2350121 | 4/1975 | Fed. Rep. of Germany ...... | 548/262 |
| 2350122 | 4/1975 | Fed. Rep. of Germany ...... | 548/262 |
| 2350123 | 4/1975 | Fed. Rep. of Germany ...... | 548/262 |
| 3018865 | 11/1981 | Fed. Rep. of Germany ...... | 548/341 |

Primary Examiner—Alton D. Rollins
Attorney, Agent, or Firm—Cushman, Darby & Cushman

[57] ABSTRACT

Compounds, having fungicidal and plant growth regulatory properties, of the formula (I):

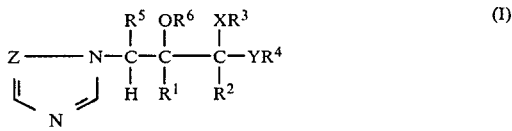

and stereoisomers thereof, wherein Z is $-CH=$ or $=N-$; $R^1$ is alkyl, cycloalkyl, alkenyl, alkynyl, optionally substituted aryl especially phenyl, or aralkyl; $R^2$ is hydrogen, alkyl, cycloalkyl, alkenyl, alkynyl, optionally-substituted aryl especially phenyl or aralkyl; $R^3$ and $R^4$, which may be the same or different, are alkyl, alkenyl, alkynyl, aryl, aralkyl, or together form a bridging group linking X and Y; $R^5$ is hydrogen, alkyl or aryl; $R^6$ is hydrogen, alkyl, alkenyl, alkynyl or acyl; and X and Y, which may be the same or different, are oxygen or sulphur; and acid salts and metal complexes thereof.

6 Claims, No Drawings

TRIAZOLYLALKANETRIOL DERIVATIVES

This invention relates to triazole and imidazole compounds useful as fungicides, to a process for preparing them, to fungicidal compositions containing them, and to methods of using them to combat fungi, especially fungal infections in plants, and to regulate plant growth.

The invention provides a compound having the general formula (I):

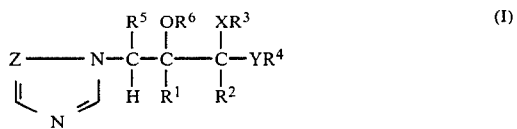

and stereoisomers thereof, wherein Z is —CH= or =N—; $R^1$ is alkyl, cycloalkyl, alkenyl, alkynyl, optionally substituted aryl especially phenyl, or aralkyl; $R^2$ is hydrogen, alkyl, cycloalkyl, alkenyl, alkynyl, optionally-substituted aryl especially phenyl or aralkyl; $R^3$ and $R^4$, which may be the same or different, are alkyl, alkenyl, alkynyl, aryl, aralkyl, or together form a bridging group linking X and Y; $R^5$ is hydrogen, alkyl or aryl; $R^6$ is hydrogen, alkyl, alkenyl, alkynyl or acyl; and X and Y, which may be the same or different, are oxygen or sulphur; and acid salts and metal complexes thereof.

The compounds of the invention contain at least one chiral centre. Such compounds are generally obtained in the form of racemic mixtures. However, these and other mixtures can be separated into the individual isomers by methods known in the art and this invention embraces such isomers.

Examples of suitable substituent groups for $R^1$, $R^2$, $R^3$, $R^4$ and $R^5$ when they represent aryl, especially phenyl, are halogen, haloalkyl, alkyl, alkoxy, nitro, phenyl and phenoxy. Suitably the aryl, especially phenyl, is unsubstituted or substituted with 1, 2 or 3 ring substituents as defined above. Examples of specific values for $R^1$, $R^2$, $R^3$, $R^4$ and $R^5$ are phenyl, 2—, 3— or 4—chlorophenyl, 2,4— or 2,6-dichlorophenyl, 2—, 3— or 4-fluorophenyl, 2—, 3— or 4-bromophenyl, 2—, 3— or 4-methoxyphenyl, 2,4-dimethoxyphenyl, 2—, 3— or 4ethoxyphenyl, 2—, 3— or 4-nitrophenyl, 2—, 3— or 4-methylphenyl, 2—, 3— or 4-trifluoromethylphenyl, 4-phenylphenyl (4-biphenylyl), 2-chloro-4-methoxyphenyl, 2-fluoro-4-methoxyphenyl, 2-chloro-4-methylphenyl and 2-fluoro-4-methylphenyl.

When any of $R^1$, $R^2$, $R^3$, $R^4$, $R^5$ and $R^6$ are alkyl, it can be a straight or branched chain alkyl group having 1 to 6, eg 1 to 4, carbon atoms; examples are methyl, ethyl, propyl (n- or iso-propyl) and butyl (n-, sec-, iso- or t-butyl). When any of $R^1$, $R^2$, $R^3$, $R^4$, $R^5$ and $R^6$ is alkenyl it may be, for example, allyl, and when alkynyl it may be, for example, propargyl. Examples of cycloalkyl substituents for $R^1$, $R^2$, $R^3$ and $R^4$ are cyclopropyl, cyclobutyl, cyclopentyl, cyclohexyl and cycloheptyl. When $R^3$ and $R^4$ form a bridging group this can contain from one to three methylene or substituted methylene groups. When $R^6$ is acyl this can be, for example, an acetyl group.

The salts can be salts with inorganic or organic acids e.g. hydrochloric, nitric, sulphuric, acetic, 4-toluenesulphonic or oxalic acid.

Suitably the metal complex is one including, as the metal, copper, zinc, manganese or iron. It preferably has the general formula:

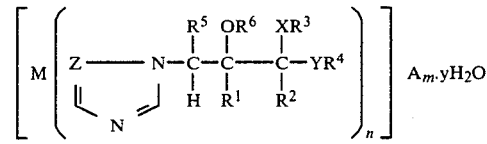

wherein Z, X, Y, $R^1$, $R^2$, $R^3$, $R^4$, $R^5$ and $R^6$ are as defined above, M is a metal, A is an anion (e.g. a chloride, bromide, iodide, nitrate, sulphate or phosphate anion), n is 2 or 4, y is 0 or an integer of 1 to 12, and m is an integer consistent with valency.

Examples of the compounds of the invention are shown in Table 1. These conform of to formula I.

TABLE I

| COMPOUND NO | $R^1$ | $R^2$ | $R^3$ | $R^4$ | $R^5$ | $R^6$ | X | Y | Z | MELTING POINT (°C.) |
|---|---|---|---|---|---|---|---|---|---|---|
| 1 | $C_6H_5$ | H | $C_2H_5$ | $C_2H_5$ | H | H | O | O | N | 69–71 |
| 2 | $C_6H_5$ | H | $C_2H_5$ | $C_2H_5$ | H | $CH_3$ | O | O | N | 88–88.5 |
| 3 | $C_6H_5$ | H | $i-C_3H_7$ | $i-C_3H_7$ | H | H | O | O | N | 73–74.5 |
| 4 | $2,4-di-Cl—C_6H_3$ | H | $C_2H_5$ | $C_2H_5$ | H | H | O | O | N | 93–94.5 |
| 5 | $4-Cl—C_6H_4$ | H | $C_2H_5$ | $C_2H_5$ | H | H | O | O | N | 90–92.5 |
| 6 | $4-Cl—C_6H_4$ | H | $i-C_3H_7$ | $i-C_3H_7$ | H | H | O | O | N | 109–110 |
| 7 | $C_6H_5$ | H | $C_2H_5$ | $C_2H_5$ | H | H | O | O | CH | 98–99 |
| 8 | $C_6H_5$ | H | $CH_2:CHCH_2$ | $CH_2:CHCH_2$ | H | H | O | O | N | oil |
| 9 | $C_6H_5$ | H | $n-C_3H_7$ | $n-C_3H_7$ | H | H | O | O | N | oil |
| 10 | $(CH_3)_3C$ | H | $CH_3$ | $CH_3$ | H | H | O | O | N | oil |
| 11 | $4-Cl—C_6H_4$ | H | $n-C_3H_7$ | $n-C_3H_7$ | H | H | O | O | N | oil |
| 12 | $2,4-di-Cl—C_6H_3$ | H | $n-C_3H_7$ | $n-C_3H_7$ | H | H | O | O | N | 116–117.5 |
| 13 | $(CH_3)_3C$ | H | $n-C_3H_7$ | $n-C_3H_7$ | H | H | O | O | N | oil |
| 14 | $(CH_3)_3C$ | H | $i-C_3H_7$ | $i-C_3H_7$ | H | H | O | O | N | oil |
| 15 | $(CH_3)_3C$ | H | $C_2H_5$ | $C_2H_5$ | H | H | O | O | N | oil |
| 16 | $2,4-di-Cl—C_6H_3$ | H | $i-C_3H_7$ | $i-C_3H_7$ | H | H | O | O | N | 117–118 |
| 17 | $C_6H_5$ | $C_6H_5$ | —$CH_2$—$CH_2$—* | | H | H | O | O | N | 145–145.5 |
| 18 | $C_6H_5$ | $C_6H_5$ | $CH_3$ | $CH_3$ | H | H | O | O | N | 144.5–146 |
| 19 | $2,4-di-Cl—C_6H_3$ | H | $CH_3$ | $CH_3$ | H | H | O | O | N | 104–104.5 |
| 20 | $2,4-di-Cl—C_6H_3$ | H | $n-C_3H_7$ | $C_2H_5$ | H | H | O | O | N | 100–101+ |
| 21 | $2,4-di-Cl—C_6H_3$ | H | $n-C_3H_7$ | $C_2H_5$ | H | H | O | O | N | 77–78+ |
| 22 | $2,4-di-Cl—C_6H_3$ | H | $n-C_3H_7$ | $CH_3$ | H | H | O | O | N | 60–61++ |
| 23 | $2,4-di-Cl—C_6H_3$ | H | $n-C_3H_7$ | $CH_3$ | H | H | O | O | N | 74–75++ |
| 24 | $(CH_3)_3C$ | H | $n-C_3H_7$ | $CH_3$ | H | H | O | O | N | oil⊕ |
| 25 | $(CH_3)_3C$ | H | $n-C_3H_7$ | $CH_3$ | H | H | O | O | N | oil⊕ |
| 26 | $2,4-di-Cl—C_6H_3$ | $CH_3$ | $CH_3CH_2$ | $CH_3CH_2$ | H | H | O | O | N | 112–114 |
| 27 | $C_6H_5$ | H | $C_2H_5$ | $C_2H_5$ | H | H | O | S | N | 80–81⊖ |
| 28 | $C_6H_5$ | H | $C_2H_5$ | $C_2H_5$ | H | H | O | S | N | oil⊖ |

TABLE I-continued

| COMPOUND NO | $R^1$ | $R^2$ | $R^3$ | $R^4$ | $R^5$ | $R^6$ | X | Y | Z | MELTING POINT (°C.) |
|---|---|---|---|---|---|---|---|---|---|---|
| 29 | 4-Cl—$C_6H_4$ | H | —$CH_2$—$CH_2$—$CH_2$—*** | | H | H | S | S | N | |
| 30 | 2,4-di-Cl—$C_6H_3$ | H | —$CH_2$—$CH_2$—$CH_2$—*** | | H | H | S | S | N | |
| 31 | 4-Cl—$C_6H_4$ | $CH_3$ | —$CH_2$—$CH_2$—$CH_2$— | | H | *** | S | S | N | |
| 32 | 2,4-di-Cl—$C_6H_3$ | $CH_3$ | —$CH_2$—$CH_2$—$CH_2$—*** | | H | H | S | S | N | |
| 33 | 2-Cl—4-$CH_3$—$C_6H_3$ | H | $CH_3$ | $CH_3$ | H | H | O | O | N | |
| 34 | 2-Cl—4-$CH_3$—$C_6H_3$ | H | $CH_3$ | $CH_3$ | H | H | O | O | CH | |
| 35 | 2-Cl—4-$CH_3$—$C_6H_3$ | H | $C_2H_5$ | $C_2H_5$ | H | H | O | O | N | 59.5–60.5 |
| 36 | 2-Cl—4-$CH_3$—$C_6H_3$ | H | $C_2H_5$ | $C_2H_5$ | H | H | O | O | CH | |
| 37 | 2,4-di-Cl—$C_6H_3$ | n-$C_4H_9$ | $C_2H_5$ | $C_2H_5$ | H | H | O | O | N | |
| 38 | 2,4-di-Cl—$C_6H_3$ | n-$C_4H_9$ | $CH_3$ | $CH_3$ | H | H | O | O | N | |
| 39 | $C_6H_5$ | H | —$CH(CH_3)CH_2CH(CH_3)$—*** | | H | H | O | O | N | oil |
| 40 | 4-Cl—$C_6H_4$ | H | $C_2H_5$ | $C_2H_5$ | H | H | O | S | N | 106–111 |
| 41 | 2,4-di-Cl—$C_6H_3$ | H | $C_2H_5$ | $C_2H_5$ | H | H | O | S | N | oil |
| 42 | 2,4-di-Cl—$C_6H_3$ | H | $CH_3$ | $CH_2CH_3$ | H | H | O | S | N | oil |
| 43 | 2,4-di-Cl—$C_6H_3$ | H | $CH_2CH_3$ | $CH_3$ | H | H | O | S | N | oil |
| 44 | 2,4-di-Cl—$C_6H_3$ | H | $CH_3$ | $CH_3$ | H | H | O | S | N | oil** |

*Groups $R^3$ and $R^4$ are joined, forming a 1,3-dioxalan
+these are diastereoisomers of one another
+ these are diastereoisomers of one another
⊕these are diastereoisomers of one another
**mixture of stereoisomers
***groups $R^3$ and $R^4$ are joined
⊖these are diastereoisomers of one another The compounds of the invention having the general formula (I):

$$R^1-\underset{\underset{R^5-CH}{|}}{\overset{\overset{OR^6}{|}}{C}}-\underset{\underset{N-Z}{|}}{\overset{\overset{XR^3}{|}}{C}}-YR^4 \quad (I)$$

(with N=N ring attached to N—Z)

wherein $R^5$ and $R^6$ are hydrogen and $R^1$, $R^2$, $R^3$, $R^4$, X, Y and Z are defined as above, can be prepared by treatment of epoxides of general formula (II):

$$R^1-\overset{O-CH_2}{\underset{C-YR^4}{C\underset{|}{\overset{XR^3}{|}}}} \quad (II)$$

wherein $R^1$, $R^2$, $R^3$, $R^4$, X and Y are as defined above, either with 1,2,4-triazole or with imidazole, each in the presence of an acid-binding agent or in the form of one of its alkali metal salts, in a convenient solvent such as dimethylformamide or acetonitrile.

Epoxides of general formula (II) can be prepared from ketones of general formula (III):

$$R^1-\overset{O}{\overset{\|}{C}}-\underset{\underset{R^2}{|}}{\overset{\overset{XR^3}{|}}{C}}-YR^4 \quad (III)$$

wherein $R^1$, $R^2$, $R^3$, $R^4$, X and Y are as defined above, by treatment with dimethylsulphonium methylide (E. J. Corey and M. Chaykovsky, *J. Amer. Chem. Soc.*, 1962, 84, 3782) or with dimethyloxosulphonium methylide (E. J. Corey and M. Chaykovsky, *J. Amer. Chem. Soc.*, 1965, 87, 1353) using methods set out in the literature.

Ketones of general formula (III) wherein $R^2$ is hydrogen can be made by selective acetalisation or thioacetalisation of glyoxals of general formula (IV):

$$R^1-\overset{O}{\overset{\|}{C}}-CHO \quad (IV)$$

wherein $R^1$ is as defined above, or by selective acetalisation or thioacetalisation of the corresponding hydrates of general formula (V):

$$R^1-\overset{O}{\overset{\|}{C}}-CH(OH)_2 \quad (V)$$

wherein $R^1$ is as defined above. Alternatively, ketones of general formula (III) wherein $R^3=R^4$ and X=Y can be made by treatment of α,α-dihaloketones of general formula (VI):

$$R^1-\overset{O}{\overset{\|}{C}}-CA_2R^2 \quad (VI)$$

wherein $R^1$ is as defined above and A is a halogen (preferably chlorine, bromine, or iodine) with a nucleophile of general formula (VII):

$$R^3XM \quad (VII)$$

wherein $R^3$ and X are as defined above and M is a metal or hydrogen, in a suitable solvent (see, for example, W. L. Evans and C. R. Parkinson, *J. Amer. Chem. Soc.*, 1913, 35, 1770, and J. Houben and W. Fischer, *Berichte*, 1931, 64, 2636).

The glyoxals (IV), the hydrates (V), and the α,α-dihaloketones (VI), can be prepared by methods set out in the literature.

In another approach, ketones of general formula (III) can be prepared by reaction of Grignard reagents of general formula (VIII):

$$R^1MgA \quad (VIII)$$

wherein $R^1$ and A are as defined above with nitriles of general formula (IX):

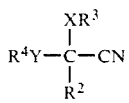

$$\begin{array}{c} XR^3 \\ | \\ R^4Y-C-CN \\ | \\ R^2 \end{array} \quad \text{(IX)}$$

wherein $R^2$, $R^3$ and $R^4$ are as defined above, followed by selective hydrolysis. Nitriles of general formula (IX) can be prepared by methods described in the chemical literature (see, for example, K. Utimoto et al, *Tetrahedron Letters*, 1981, 22, 4297).

Alternatively, ketones of general formula (III) can be prepared by reaction between Grignard reagents of general formula (VIII) and aldehydes of general formula (X):

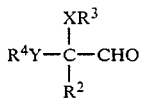

$$\begin{array}{c} XR^3 \\ | \\ R^4Y-C-CHO \\ | \\ R^2 \end{array} \quad \text{(X)}$$

wherein $R^2$, $R^3$, $R^4$, X and Y are as defined above, followed by oxidation of the resulting alcohol (using, for example, pyridinium dichromate in dimethylformamide: see E. J. Corey and G. Schmidt, *Tetrahedron Letters*, 1979, 399). Aldehydes of general formula (X) can be prepared by methods described in the literature (for example, by reduction of the corresponding carboxylic ester with di-isobutylaluminium hydride).

Ketones of general formula (III) wherein $R^3$ and $R^4$ are different and X is oxygen can be made by treating halides of general formula (XI):

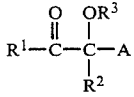

$$\begin{array}{c} O \quad OR^3 \\ \| \quad | \\ R^1-C-C-A \\ | \\ R^2 \end{array} \quad \text{(XI)}$$

wherein $R^1$, $R^2$, $R^3$ and A are as defined above, with an alcohol or thiol of general formula (XII):

$$R^4YH \quad \text{(XII)}$$

wherein $R^4$ and Y are as defined above, in the presence of a suitable base such as pyridine or triethylamine.

Halides of general formula (XI) can be prepared from ketones of general formula (III) in which $R^3$ and $R^4$ are the same and X and Y are both oxygen by treatment with an acetyl halide (preferably acetyl chloride or acetyl bromide) in the presence of a suitable catalyst (preferably copper bronze) if necessary, either as neat reactants or in a suitable solvent (see, for example, British Pat. No. 1563199, filed Sept. 10, 1975). Alternatively, the halides of general formula (XI) can be prepared from ketones of general formula (XIII):

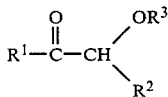

$$\begin{array}{c} O \quad\quad OR^3 \\ \| \quad\quad / \\ R^1-C-CH \\ \quad\quad\backslash \\ \quad\quad R^2 \end{array} \quad \text{(XIII)}$$

wherein $R^1$, $R^2$ and $R^3$ are defined above, using, for example, sulphuryl chloride (see, for example, L. Duhamel, J. Chauvin, and A. Messier, *Tetrahedron Letters*, 1980, 21 4171).

Halides of general formula (XI) are usually unstable and, following formation, are usually treated in situ with the appropriate base plus alcohol or thiol.

The invention, in a further aspect, provides, as novel intermediates, compounds of the formulae (II), (III), (IX), (X), (XI) and (XIII) as defined.

Compounds of general formula (I) wherein $R^6$ is not hydrogen can be prepared from the corresponding compounds wherein $R^6$ is hydrogen by successive treatment with a base (preferably sodium hydride) and a suitable alkyl, alkenyl, alkynyl, or acyl halide (preferably chloride, bromide, or iodide) in a suitable solvent such as dimethylformamide or tetrahydrofuran.

The salts and metal complexes of the compounds of general formula (I) can be prepared from the latter in known manner. For example, the complexes can be made by reacting the uncomplexed compound with a metal salt in a suitable solvent.

The compounds, salts and metal complexes are active fungicides, particularly against the diseases:

*Piricularia oryzae* on rice

*Puccinia recondita*, *Puccinia striiformis* and other rusts on wheat, *Puccinia hordei*, *Puccinia striiformis* and other rusts on barley, and rusts on other hosts e.g. coffee, apples, vegetables and ornamental plants

*Plasmopara viticola* on vines

*Erysiphe graminis* (powdery mildew) on barley and wheat and other powdery mildews on various hosts such as *Sphaerotheca fuliginea* on cucurbits (e.g. cucumber), *Podosphaera leucotricha* on apples and *Uncinula necator* on vines

*Helminthosporium* spp. and *Rhynchosporium* spp. on cereals

*Cercospora arachidicola* on peanuts and other *Cercospora* species on for example sugar beet, bananas and soya beans

*Botrytis cinerea* (grey mould) on tomatoes, strawberries, vines and other hosts

*Phytophthora infestans* (late blight) on tomatoes

*Venturia inaequalis* (scab) on apples

Some of the compounds have also shown a broad range of activities against fungi in vitro. They have activity against various post-harvest diseases on fruit (e.g. *Penicillium digatatum* and italicum on oranges and *Gloeosporium musarum* on bananas). Further some of the compounds are active as seed dressings against: *Fusarium* spp., *Septoria* spp., *Tilletia* spp. (i.e. bunt, a seed borne disease of wheat), *Ustilago* spp., *Helminthosporium* spp., on cereals, *Rhizoctonia solani* on cotton and *Corticium sasakii* on rice.

The compounds can move acropetally in the plant tissue. Moreover, the compounds can be volatile enough to be active in the vapour phase against fungi on the plant.

The compounds, and their derivatives as defined above, also have plant growth regulating activities.

The plant growth regulating effects of the compounds are manifested as, for example, by a stunting or dwarfing effect on the vegetative growth of woody and herbaceous mono- and di-cotyledonous plants. Such stunting or dwarfing may be useful, for example, in peanuts, cereals and soya bean where reduction in stem growth may reduce the risk of lodging and may also permit increased amounts of fertiliser to be applied. The stunting of woody species is useful in controlling the growth of undergrowth under power lines etc. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. Examples of suitable grasses are *Stenotaphrum secundatum* (St. Augustine grass), *Cynosurus cristatus, Lolium multiflorum* and *perenne, Agrostis tenuis, Cynodon dactylon* (Bermuda grass), *Dactylis glomerata, Festuca* spp. (e.g. *Festuca rubra*) and *Poa* spp. (e.g. *Poa pratense*). The compounds may stunt grasses without significant phytotoxic effects and without deleteriously affecting the appearance (particularly the colour) of the grass; this makes such compounds attractive for use on ornamental lawns and on grass verges. They may also have an effect on flower head emergence in, for example, grasses. The compounds can also stunt weed species present in the grasses; examples of such weed species are sedges (e.g. *Cyperus* spp.) and dicotyledonous weeds (e.g. daisy, plantain, knotweed, speedwell, thistle, docks and ragwort). The growth of non-crop vegetation (e.g. weeds or cover vegetation) can be retarded thus assisting in the maintenance of plantation and field crops. In fruit orchards, particularly orchards subject to soil erosion, the presence of grass cover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful for example for improving the quality of a sward by preferential suppression of the growth of undesirable species.

The dwarfing may also be useful in miniaturising ornamental, household, garden and nursery plants (e.g. poinsettias, chrysanthemums, carnations, tulips and daffodils).

As indicated above, the compounds can also be used to stunt woody species. This property can be used to control hedgerows or to shape fruit trees (e.g. apples). Some coniferous trees are not significantly stunted by the compounds so the compounds could be useful in controlling undesirable vegetation in conifer nurseries.

The plant growth regulating effect may (as implied) above) manifest itself in an increase in crop yield.

In the potato, vine control in the field and inhibition of sprouting in the store may be possible.

Other plant growth regulating effects caused by the compounds include alteration of leaf angle and promotion of tillering in monocotyledonous plants. The former effect may be useful for example in altering the leaf orientation of, for example, potato crops thereby letting more light into the crops and inducing an increase in phytosynthesis and tuber weight. By increasing tillering in monocotyledonous crops (e.g. rice), the number of flowering shoots per unit area may be increased thereby increasing the overall grain yield of such crops. In grass swards an increase in tillering could lead to a denser sward which may result in increased resilience in wear.

The treatment of plants with the compounds can lead to the leaves developing a darker green colour.

The compounds may inhibit, or at least delay, the flowering of sugar beet and thereby may increase sugar yield. They may also reduce the size of sugar beet without reducing significantly the sugar yield thereby enabling an increase in planting density to be made. Similarly in other root crops (e.g. turnip, swede, mangold, parsnip, beetroot, yam and cassava) it may be possible to increase the planting density.

The compounds could be useful in restricting the vegetative growth of cotton thereby leading to an increase in cotton yield.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below snow cover during the cold weather. Further the compounds may cause drought or cold resistance in certain plants.

When applied as seed treatments at low rates the compound can have a growth stimulating effect on plants.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. However, on certain plants even application rates within these ranges may give undesired phytotoxic effects. Routine tests may be necessary to determine the best rate of application of a specific compound for any specific purpose for which it is suitable.

The compounds are also useful for the treatment of candidiasis and human dermatophyte infections.

The compounds may be used as such for fungicidal or plant growth regulating purposes but are more conveniently formulated into compositions for such usage. The invention thus provides also a fungicidal, or plant growth regulating composition comprising a compound of general formula (I) or a salt or complex thereof as hereinbefore defined, and a carrier or diluent.

The invention also provides a method of regulating the growth of plants, which method comprises applying to the plant, to seed of the plant, or to the locus of the plant or seed, a compound, or a salt or complex thereof, as hereinbefore defined.

The invention further provides a method of combating fungal diseases in a plant, which method comprises applying to the plant, to seed of the plant or to the locus of the plant or seed, a compound, or a salt or complex thereof, as hereinbefore defined.

The compounds, salts and complexes can be applied in a number of ways, for example they can be formulated or unformulated, directly to the foliage of a plant, to seeds or to other medium in which plants are growing or are to be planted, or they can be sprayed on, dusted on or applied as a cream or paste formulation, or they can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition.

The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form.

By including suitable additives, for example additives for improving the distribution, adhesive power and resistance to rain on treated surfaces, the different compositions can be better adapted for various utilities.

The compounds can be used as mixtures with fertilisers (e.g. nitrogen—, potassium— or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising the compound of general formula (I) or a salt or metal complex thereof.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s). These agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl—and triisopropylnaphthalene sulphonates).

Suitable non-ionic agents are the condensation products of ethylene oxide with fatty alcohols such as oleyl or cetyl alcohol, or with alkyl phenols such as octyl—or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient(s). These concentrates suitably contain organic acids (e.g. alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, e.g. compounds having similar or complementary fungicidal activity or compounds having plant growth regulating, herbicidal or insecticidal activity.

The other fungicidal compound can be for example one which is capable of combating ear diseases of cereals (e.g. wheat) such as *Septoria, Gibberella* and *Helminthosporium* spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are imazalil, benomyl, carbendazim, thiophanate-methyl, captafol, captan, sulphur, triforine, dodemorph, tridemorph, pyrazophos, furalaxyl, ethirimol, dimethirimol, bupirimate, chlorothalonil, vinclozolin, procymidone, iprodione, metalaxyl, forsetyl-aluminium, carboxin, oxycarboxin, fenarimol, nuarimol, fenfuram, methfuroxan, nitrotal-isopropyl, triadimefon, thiabendazole, etridiazole, triadimenol, biloxazol, dithianon, binapacryl, quinomethionate, guazitine, dodine, fentin acetate, fentin hydroxide, dinocap, folpet, dichlorfluanid, ditalimphos, kitazin, cycloheximide, dichlobutrazol, a dithiocarbamate, a copper compound, a mercury compound, 2-(1-cyano-2-methoxyiminoacetyl)-3-ethyl urea, fenapanil, ofurace, propiconazole, etaconazole and fenpropemorph.

The compounds of general formula (I) can be mixed with soil, peat or other rooting media for the protection of plants against seed-borne, soil-borne or foliar fungal diseases.

Suitable insecticides are Pirimor, Croneton, dimethoate, Metasystox and formothion.

The other plant growth regulating compound can be one which controls weeds or seedhead formation, improves the level or longevity of the plant growth regulating activity of the compounds of general formula (I), selectively controls the growth of the less desirable plants (e.g. grasses) or causes the compound of general formula (I) to act faster or slower as a plant growth regulating agent. Some of these other agents will be herbicides.

Examples of suitable plant growth regulating compounds are the gibberellins (e.g. $GA_3$, $GA_4$ or $GA_7$, the auxins (e.g. indoleacetic acid, indole-butyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acids (e.g. triiodobenzoic acid), morphactins (e.g. chlorfluorecol), maleic hydrazide, glyphosate, glyphosine long chain fatty alcohols and acids, dikegulac, fluoridamid, mefluidide, substituted quaternary ammonium and phosphonium compounds (e.g. chlormequat or chlorphonium), ethephon, carbetamide, methyl-3,6-dichloranisate, daminozide, mepiquat chloride, asulam, abscissic acid, isopyrimol, 1(4-chlorophenyl)-4,6-dimethyl-2-oxo-1,2-dihydropyridine-3-carboxylic acid, hydroxybenzonitriles (e.g. bromoxynil), difenzoquat, benzoylpropethyl, and 3,6-dichloropicolinic acid.

The following Examples illustrates the invention; the temperatures are given in degrees Centigrade (°C.).

EXAMPLE 1

This Example illustrates the preparation of 1,1-diethoxy-2-hydroxy-2-phenyl-3-(1,2,4-triazol-1-yl)propane (compound number 1 of Table I).

Phenylglyoxal monohydrate (12.25 g) and 4-toluenesulphonic acid monohydrate (0.75 g) were dissolved in a mixture of ethanol (30 ml) and 40°–60° petrol (40 ml) and refluxed for 14 hours under a Dean and Stark apparatus. During reflux the lower layer of the azeotrope was removed and the volume of solvent in the reaction vessel was maintained by addition of further ethanol and petrol. The solvent was removed under reduced pressure and the residue was taken up in diethyl ether and washed successively with aqueous sodium bicarbonate and water, then dried over magnesium sulphate, and concentrated to give a yellow oil (16.0 g). The crude product was flushed through a column of neutral alumina using dichloromethane/40°–60° petrol (1:1) as solvent to remove traces of the hemiacetal, and gave phenylglyoxal diethyl acetal (13.50 g, 18%) as a pale yellow mobile liquid.

A suspension of sodium hydride (1.71 g) in dry dimethylsulphoxide (DMSO: 80 ml) was stirred at 50° under a nitrogen atmosphere for 2.5 hours. The resulting clear solution was diluted with dry tetrahydrofuran (THF: 100 ml) and cooled in an ice-salt bath. Solutions of trimethylsulphonium iodide (14.56 g) in DMSO (80 ml) and phenylglyoxal diethyl acetal (13.50 g) in THF (80 ml) were added successively to the stirred dimsyl sodium solution, maintaining the temperature of the reaction mixture at about 0°. After 15 minutes the cooling bath was removed and after a further hour the reaction mixture was diluted with water and extracted with ether. The combined extracts were washed with water, dried over magnesium sulphate, and concentrated to give 1,1-diethoxy-2-phenyl-2,3-epoxypropane (13.23 g, 92%) as a yellow liquid. Short path distillation of a small sample (224 mg) gave a colourless liquid (190 mg), boiling point 185°–190° (10 torr), (found: C, 70.12; H, 7.93% $C_{13}H_{18}O_3$ requires C, 70.25; H, 8.16%).

A solution of 1,1-diethoxy-2-phenyl-2,3-epoxypropane (8.54 g) in dry dimethylformamide (DMF: 40 ml) was added to a stirred solution of sodium triazole [from 1,2,4-triazole (2.92 g) and sodium hydride (1.02 g)] in DMF (80 ml) under nitrogen, and the mixture was heated at 54° for 5 hours. Water was added, the mixture was extracted with ether, and the combined extracts were washed with water, dried over magnesium sulphate, and concentrated to give a viscous yellow oil (7.89 g) which partially crystallised on standing. The crystals were washed with 40°–60° petrol and dried to give the title compound (4.86 g, 43%) as colourless short needles, m.p. 69°–71°, (found: C, 61.99; H, 7.21; N, 14.22%, $C_{15}H_{21}N_3O_3$ requires C, 61.84; H, 7.26; N, 14.42%).

EXAMPLE 2

This Example illustrates the preparation of 1,1-diethoxy-2-methoxy-2-phenyl-3-(1,2,4-triazol-1-yl)propane (compound 2 of Table I). 1,1-Diethoxy-2-hydroxy-2-phenyl-3-(1,2,4-triazol-1-yl)propane (0.98 g) was added to a stirred suspension of sodium hydride (0.12 g) in dry dimethylformamide (35 ml) under nitrogen and at room temperature. After 1.5 hours the mixture was cooled in an ice-salt bath and methyl iodide (0.7 ml) was added. The mixture was allowed to stand at room temperature overnight, then water was added and it was extracted with ether. The combined extracts were washed with water, dried over magnesium sulphate, and concentrated to give an off-white solid (0.81 g) which crystallised from diethyl ether to give the title compound (0.54 g, 53%) as colourless prisms, m.p. 88°–88.5°, (found: C, 63.11; H, 7.49; N, 13.78%. $C_{16}H_{23}N_3O_3$ requires C, 62.93; H, 7.59; N, 13.76%).

EXAMPLE 3

This Example illustrates the preparation of 1,1-diethoxy-2-hydroxy-2-(2,4-dichlorophenyl)-3-(1,2,4-triazol-1-yl)propane (compound number 4 of Table I).

By the procedure described for the preparation of 1,1-diethoxy-2-phenyl-2,3-epoxypropane (see Example 1), sodium hydride (0.14 g), trimethylsulphonium iodide (1.21 g), and 2,4-dichlorophenylglyoxal diethyl acetal (1.49 g), gave 1,1-diethoxy-2-(2,4-dichlorophenyl)-2,3-epoxypropane (1.40 g, 90%) as a yellow liquid.

By the procedure described for the preparation of 1,1-diethoxy-2-hydroxy-2-phenyl-3-(1,2,4-triazol-1-yl)-propane (see Example 1), 1,1-diethoxy-2-(2,4-dichlorophenyl)-2,3-epoxypropane (1.22 g), 1,2,4-triazole (0.32 g) and sodium hydride (0.11 g) gave a crude product (1.22 g) as a viscous orange oil. This was chromatographed on a column of silica gel using diethyl ether as solvent to give the title compound (0.63 g, 42%) as a colourless crystalline salid, m.p. 93°–94.5°, (found: C, 50.17; H, 5.27; N, 11.32%. $C_{15}H_{19}Cl_2N_3O_3$ requires C, 50.01; H, 5.32; N, 11.66%).

EXAMPLE 4

This Example illustrates the preparation of 1-methoxy-1-(1-propoxy)-2-hydroxy-2-(2,4-dichlorophenyl)-3-(1,2,4-triazol-1-yl)propane. (Compound numbers 22 and 23 of Table I).

Acetyl bromide (2.06 g) was added to α,α-di-(1-propoxy)-2,4-dichloroacetophenone (2.56 g) with stirring (mild exotherm). After 15 minutes, dry diethyl ether (50 ml), triethylamine (1.69 g), dry diethyl ether (30 ml), and dry methanol (10 ml) were added successively to the reaction mixture which was then warmed at 30° for 10 minutes. The mixture was poured into water and extracted with ether. The extracts were washed successively with aqueous sodium bicarbonate and water, dried over magnesium sulphate, concentrated under reduced pressure, and purified by chromatography on a column of silica gel (eluting with 15% ether in 40°-60° petrol) to give α-methoxy-α-(1-propoxy)-2,4-dichloroacetophenone (1.21 g, 52%) as an oil, $^1$H nmr (CDCl$_3$): δ 3.49 (3H, singlet, CH$_3$O), 5.18 [1H, singlet, C$\underline{H}$(OCH$_3$)(OC$_3$H$_7$)].

By the procedure described for the preparation of 1,1-diethoxy-2-phenyl-2,3-epoxypropane (see Example 1), sodium hydride (0.115 g), trimethylsulphonium iodide (0.98 g), and α-methoxy-α-(1-propoxy)-2,4-dichloroacetophenone (1.21 g) gave 1-methoxy-1-(1-propoxy)-2-(2,4-dichlorophenyl)-2,3-epoxypropane (0.94 g, 74%) as a yellow oil.

By the procedure described for the preparation of 1,1-diethoxy-2-hydroxy-2-phenyl-3-(1,2,4-triazol-1-yl)propane (see Example 1), 1-methoxy-1-(1-propoxy)-2-(2,4-dichlorophenyl)-2,3-epoxypropane (0.94 g), 1,2,4-triazole (0.247 g), and sodium hydride (0.085 g) gave a crude product (1.00 g) which was purified by chromatography on a column of silica gel (eluting with ethyl acetate: 40°-60° petrol, 4:1) to give the individual diastereoisomers of the title compound:

Isomer A: White solid (298 mg, 26%), m.p. 60°-61°, R$_f$(ethyl acetate) ca. 0.3, $^1$H nmr (CDCl$_3$):δ 0.96 (3H, triplet, J 8 Hz, C$\underline{H}$$_3$CH$_2$CH$_2$O), 3.20 (3H, singlet, CH$_3$O).

Isomer B: White solid (291 mg, 25%), m.p. 74°-75°, R$_f$(ethyl acetate) ca. 0.2, $^1$H nmr (CDCl$_3$): δ 0.64 (3H, triplet, J 8 Hz, C$\underline{H}$$_3$CH$_2$CH$_2$O), δ 3.50 (3H, singlet, CH$_3$O).

EXAMPLE 5

This Example illustrates the preparation of 1,1-diethoxy-2-hydroxy-2-(2-chloro-4-methylphenyl)-3-(1,2,4-triazol-1-yl)propane (compound number 35 of Table I).

A solution of diethoxyacetonitrile (6.45 g: prepared from triethylorthoformate, trimethylsilyl cyanide, and boron trifluoride etherate: K. Utimoto et al., *Tetrahedron Letters*, 1981, 22, 4279) in dry ether (50 ml ) was added to a stirred solution of 2-chloro-4-methylphenylmagnesium iodide [from 2-chloro-4-methyl-iodobenzene (12.70 g) and magnesium (1.44 g)] in dry ether (150 ml) (mild exotherm). The stirred mixture was heated at 45° for 3 hours, then allowed to cool. Dilute hydrochloric acid was added carefully with stirring (exotherm) and the mixture was stirred for 5 minutes, then extracted with ether. The extracts were washed successively with water, aqueous sodium bicarbonate (X2), and water, then treated with magnesium sulphate and charcoal, filtered, and concentrated under reduced pressure to give an orange liquid (11.595 g). The crude product was purified on a column of silica gel (eluting with 10% ether in 40°-60° petrol) and gave 2-chloro-4-methylphenylglyoxal diethyl acetal (7.58 g, 59%) as a pale yellow liquid, $^1$H nmr (CDCl$_3$): δ 2.36 (3H, singlet, aromatic methyl), δ 5.27 [1H, singlet, C$\underline{H}$(OC$_2$H$_5$)$_2$].

By the procedure described for the preparation of 1,1-diethoxy-2-phenyl-2,3-epoxypropane (see Example 1), sodium hydride (0.713 g), trimethylsulphonium iodide (0.98 g), and 2-chloro-4-methylphenylglyoxal diethyl acetal (6.945 g) gave 1,1-diethoxy-2-(2-chloro-4-methlphenyl)-2,3-epoxypropane (7.111 g, 97%) as a pale yellow oil.

By the procedure described for the preparation of 1,1-diethoxy-2-hydroxy-2-phenyl-3-(1,2,4-triazol-1-yl)propane (see Example 1), 1,1-diethoxy-2-(2-chloro-4-methylphenyl)-2,3-epoxypropane (4.00 g), 1,2,4-triazole (1.32 g) and sodium hydride (0.426 g) gave, as a crude product, a viscous pale yellow oil (4.391 g). Chromatography on a column of silica gel (eluting with diethyl ether) followed by trituration with 40°-60° petrol gave the title compound (2.457 g, 49%) as a pure white free-flowing solid, m.p. 56°-58°. An analytical sample crystallised from a mixture of ether and 40°-60° petrol as colourless flakes, m.p. 59.5°-60.5° (found: C, 56.62; H, 6.25; N, 12.75%. $C_{16}H_{22}ClN_3O_3$ requires C, 56.55; H, 6.53; N, 12.37%).

EXAMPLE 6

The compounds were tested against a variety of foliar fungal diseases of plants. The technique employed was as follows.

The plants were grown in John Innes Potting Compost (No 1 or 2) in 4 cm diameter minipots. A layer of fine sand was placed at the bottom of the pots containing the dicotyledonous plants to facilitate uptake of test compound by the roots. The test compounds were formulated either by bead milling with aqueous Dispersol T or as a solution in acetone or acetone/ethanol which was diluted to the required concentration immediately before use. For the foliage diseases, suspensions (100 ppm active ingredient) were sprayed on to the soil. Exceptions to this were the tests on *Botrytis cinerea*, *Plasmopara viticola* and *Venturia inaequalis*. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the diseases. An exception was the test on *Erysiphe graminis* in which the plants were inoculated 24 hours before treatment. After inoculation, the plants were put into an appropriate environment to allow infection to take place and then incubated until the disease was ready for assessment. The period between inoculation and assessment varied from four to fourteen days according to the disease and environment.

The disease control was recorded by the following grading:

4 = no disease
3 = trace—5% of disease on untreated plants
2 = 6–25% of disease on untreated plants
1 = 26–59% of disease on untreated plants
0 = 60–100% of disease on untreated plants The results are shown in Table II.

TABLE II

| COMPOUND NUMBER | PUCCINIA RECONDITA (WHEAT) | ERYSIPHE GRAMINIS (BARLEY) | PIRICULARIA ORYZAE (RICE) | PLASMOPARA VITICOLA (VINE) | PHYTOPHTHORA INFESTANS (TOMATO) | BOTRYTIS CINEREA (GRAPE) | CERCOSPORA ARACHIDICOLA (PEANUT) | VENTURIA INAEQUALIS (APPLE) |
|---|---|---|---|---|---|---|---|---|
| 1 | 4 | 4 | — | 0 | — | 0 | 4 | 4 |
| 2 | 4 | 4 | — | 0 | — | 0 | 3 | 4 |
| 3 | 4 | 4 | — | 0 | — | 0 | 3 | 4 |
| 4 | 4 | 4 | — | 0 | — | 0 | 3 | 4 |
| 5 | 4 | 4 | — | 0 | — | 0 | 3 | 3 |
| 6 | 4 | 4 | — | 0 | — | 0 | 4 | 4 |
| 7 | 4 | 4 | — | 0 | — | 0 | 3 | 0 |
| 8 | 4 | 4 | — | 0 | — | 0 | 4 | 4 |
| 9 | 4 | 4 | — | 0 | — | 3 | 4 | 4 |
| 10 | 4 | 4 | — | 0 | — | 2 | 4 | 4 |
| 11 | 4 | 4 | — | — | — | 0 | 4 | 4 |
| 12 | 4 | 4 | — | 0 | — | 0 | 4 | 4 |
| 13 | 4 | 4 | — | 0 | — | 0 | 4 | 4 |
| 14 | 4 | 4 | — | 0 | — | 0 | 4 | 4 |
| 15 | 4 | 4 | — | 0 | — | 0 | 4 | 4 |
| 16 | 4 | 4 | — | 0 | — | 0 | 4 | 4 |
| 17 | | | | | | | | |
| 18 | 4 | 4 | 3 | 0 | — | 0 | 4 | 4 |
| 19 | 4 | 4 | 2 | 3 | — | 0 | 3 | 4 |
| 20 | 4 | 4 | 3 | 0 | — | 0 | 4 | 4 |
| 21 | 4 | 4 | 3 | 0 | — | 0 | 3 | 4 |
| 22 | 4 | 4 | 4 | 0 | — | 0 | 3 | 4 |
| 23 | 4 | 4 | 3 | 0 | — | 0 | 4 | 4 |
| 24 | 4 | 4 | 3 | 0 | — | 4 | 3 | 4 |
| 25 | 4 | 4 | 3 | 0 | — | 4 | 2 | 4 |
| 26 | 4 | 4 | 4 | 1 | — | 4 | 4 | 4 |
| 27 | 4 | 4 | 3 | 0 | — | 4 | 4 | 4 |
| 28 | 4 | 4 | 4 | — | — | 4 | 4 | 4 |
| 29 | | | | | | | | |
| 30 | | | | | | | | |
| 31 | | | | | | | | |
| 32 | | | | | | | | |
| 33 | | | | | | | | |
| 34 | | | | | | | | |
| 35 | 4 | 4 | 3 | 0 | — | 0 | 4 | 4 |
| 36 | | | | | | | | |
| 37 | | | | | | | | |
| 38 | | | | | | | | |
| 39 | 4 | 4 | 0 | 0 | — | 0 | 4 | 4 |
| 40 | | | | | | | | |
| 41 | | | | | | | | |
| 42 | | | | | | | | |
| 43 | | | | | | | | |
| 44 | | | | | | | | |

"—" means "not tested"

EXAMPLE 7

This Example illustrates the plant growth regulating properties of the compounds. The compounds were applied as an overall spray of an emulsifiable concentrate diluted to give the concentrations shown in Table III. The plants were grown in 3" pots in peat compost and sprayed at the 2 leaf stage. Plant growth regulating effects were assessed 12 days after application of the compounds. Retardation of growth was scored on a 0–3 scale where:

1 = 0–30% retardation
2 = 31–75% retardation
3 = 75% retardation

Additional plant growth regulating properties are indicated as follows:

G = darker green leaf colour
A = apical effect
T = tillering effect

The results are shown in Table III. If no figure is given the compound was substantially inactive as a stunting agent

TABLE III

| COMPOUND | DAT | RATE (ppm) | AT | CC | DA | LT | SB | TO | SY | CT | MZ | WW | BR |
|---|---|---|---|---|---|---|---|---|---|---|---|---|---|
| 1 | 12 | 4000 | 2G | 2G | 2G | 2G | 2G | 2 | 2GA | 3A | | | |
| 2 | 13 | 4000 | 1 | 1 | | 2G | G | 3G | | 3A | | 1 | |
| 3 | 12 | 4000 | 1 | 1 | 1 | 2 | 2A | 2AT | 2G | | 3 | 2 | |
| 4 | 12 | 4000 | 1 | 2 | 1 | 3G | 2GA | 3GA | 3A | | | 2 | 2 |
| 5 | 12 | 4000 | 1H | 3 | 3 | 3GA | 3G | 3GAT | 2G | 2A | 3 | 1 | |
| 6 | 12 | 4000 | 2 | 2 | 2 | 3GA | 3GA | 3GA | 2G | 1 | | | |
| 7 | 19 | 4000 | | | | 3 | 1 | | 1 | 1 | T | | |
| 8 | 19 | 4000 | 1 | 1 | | 3G | 2G | 1 | 2AT | 3GAT | | 2 | |
| 9 | 19 | 4000 | 2 | 2 | 2 | 2 | 2GA | 2AT | 3AT | 2GA | 3 | | |
| 10 | 19 | 4000 | | | | 1 | 1 | 1G | 2G | | | | |
| 11 | 19 | 4000 | 1 | 1 | 1 | 2 | 3G | 1T | 2GT | 1 | 3 | 1 | 1 |
| 12 | 19 | 4000 | 1 | G | 1 | 1 | 2 | 1 | 1G | 1G | | 2 | 1 |

TABLE III-continued

| COMPOUND | DAT | RATE (ppm) | AT | CC | DA | LT | SB | TO | SY | CT | MZ | WW | BR |
|---|---|---|---|---|---|---|---|---|---|---|---|---|---|
| 13 | 19 | 4000 | 1G | G | 1 | 1 | 2G | 1 | | | 2 | 1 | 1 |
| 15 | 19 | 4000 | | G | | 2 | 1 | 1G | 3GAT | 1G | | 1 | |
| 16 | 15 | 4000 | 1 | 1 | 1 | 1 | 3G | 2G | 2G | 2GA | 1 | 1GT | T |
| 17 | 19 | 4000 | | | | | 1 | 1 | 2 | | | | |
| 19 | 19 | 4000 | 2G | 1G | 1G | 1 | 3G | 2GA | 2AT | 1 | 1G | 1GT | 1G |
| 24 | 19 | 4000 | 1 | | 2 | 1 | 1G | 1G | 2GT | 2GT | 1 | 2 | 1 |
| 25 | 19 | 4000 | 1 | 2 | 2 | 1 | G | 2GT | 2GT | 2GAT | | 2T | 1 |

Key to test species in Table III
AT *Agrostis tenuis*
CC *Cynosurus cristatus*
DA *Dactylis glomerata*
LT *Lactuca sativa*
SB *Beta vulgaris*
TO *Lycopersicon esculentum*
SY *Glycine max*
CT *Gossypium hirsutum*
MZ *Zea mays*
WW *Triticum aestivum*
BR *Hordeum vulgare*

What is claimed is:

1. A compound selected from compounds having the formula (I):

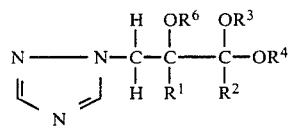

and stereoisomers thereof, wherein $R^1$ is alkyl having from 1 to 6 carbon atoms, or phenyl substituted with halogen atoms or alkyl of 1 to 6 carbons; $R^2$ is hydrogen, alkyl having from 1 to 6 carbon atoms or phenyl; $R^3$ and $R^4$, which may be the same or different, are alkyl or alkenyl each having up to 6 carbon atoms, or together form an alkylene bridging group containing from 1 to 3 carbon atoms between the two oxygen atoms and which may be optionally substituted with methyl groups; $R^6$ is hydrogen or alkyl having from 1 to 6 carbon atoms and acid salts and metal complexes thereof.

2. A compound selected from compounds having the formula:

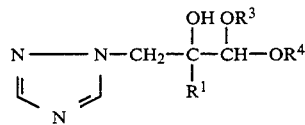

amd stereoismers thereof, wherein $R^1$ is phenyl, 4-chlorophenyl or 2,4-dichlorophenyl; and $R^3$ and $R^4$ are alkyl groups containing from 1 to 3 carbon atoms; and acid salts and metal complexes thereof.

3. The compounds:

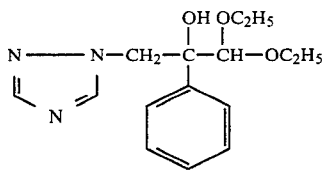

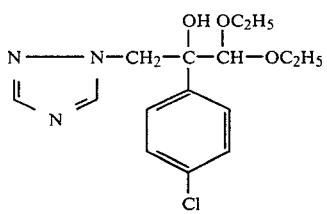

and

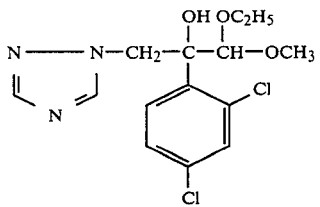

4. A fungicidal, or plant growth regulating composition comprising an effective amount of a compound of general formula (I) as defined in claim 1, and a carrier or diluent.

5. A method of regulating the growth of plants, which comprises applying to the plant, to seed of the plant, or to the locus of the plant or seed, an effective amount of a compound as defined in claim 1.

6. A method of combating fungal diseases in a plant, which method comprises applying to the plant, to seed of the plant or to the locus of the plant or seed, an effective amount of a compound, as defined in claim 1.

* * * * *